United States Patent
Blanchot et al.

(10) Patent No.: US 10,759,732 B2
(45) Date of Patent: Sep. 1, 2020

(54) PROCESS FOR PRODUCING (METH)ACRYLATES FROM GLYCEROL CARBONATE

(71) Applicant: BASF SE, Ludwigshafen am Rhein (DE)

(72) Inventors: Mathieu Blanchot, Ludwigshafen am Rhein (DE); Uwe Meisenburg, Ludwigshafen am Rhein (DE); Steffen Maurer, Ludwigshafen am Rhein (DE); Jochen Petzoldt, Ludwigshafen am Rhein (DE); Tobias Hoefener, Düsseldorf-Holthausen (DE); Boris Breitscheidel, Ludwigshafen am Rhein (DE); Andrea Misske, Ludwigshafen am Rhein (DE); Friederike Fleischhaker, Ludwigshafen am Rhein (DE); Martin Kaller, Ludwigshafen am Rhein (DE); Christoph Fleckenstein, Ludwigshafen am Rhein (DE); Ulrik Stengel, Ludwigshafen am Rhein (DE); Ritesh Nair, Ludwigshafen am Rhein (DE)

(73) Assignee: BASF SE (DE)

( * ) Notice: Subject to any disclaimer, the term of this patent is extended or adjusted under 35 U.S.C. 154(b) by 0 days.

(21) Appl. No.: 16/639,174

(22) PCT Filed: Aug. 16, 2018

(86) PCT No.: PCT/EP2018/072166
§ 371 (c)(1),
(2) Date: Feb. 14, 2020

(87) PCT Pub. No.: WO2019/034716
PCT Pub. Date: Feb. 21, 2019

(65) Prior Publication Data
US 2020/0231528 A1    Jul. 23, 2020

(30) Foreign Application Priority Data
Aug. 17, 2017 (EP) .................................. 17186588

(51) Int. Cl.
*C07C 67/24* (2006.01)
*C07D 317/36* (2006.01)

(52) U.S. Cl.
CPC ............ *C07C 67/24* (2013.01); *C07D 317/36* (2013.01)

(58) Field of Classification Search
CPC .............................. C07C 67/24; C07D 317/36
See application file for complete search history.

(56) References Cited

U.S. PATENT DOCUMENTS

| 5,359,094 A | 10/1994 | Teles et al. |
| 6,025,504 A | 2/2000 | Claude et al. |
| 7,414,147 B2 | 8/2008 | Schmitt et al. |
| 2011/0201828 A1 | 8/2011 | Prochazka et al. |

FOREIGN PATENT DOCUMENTS

| DE | 10355830 A1 | 6/2005 |
| EP | 0582201 A2 | 2/1994 |
| EP | 0739888 A1 | 10/1996 |
| EP | 0955298 A1 | 11/1999 |
| WO | WO-2010043581 A1 | 4/2010 |
| WO | WO-2010106324 A1 | 9/2010 |
| WO | WO-2011042288 A1 | 4/2011 |
| WO | WO-2013129486 A1 | 9/2013 |

OTHER PUBLICATIONS

Bassam, N., et al., "Aza-Michael versus aminolysis reactions of glycerol carbonate acrylate", Green Chemistry, vol. 15, No. 7, (2013), pp. 1900-1909.
International Preliminary Examination Report for PCT/EP2018/072166 dated Jul. 25, 2019 with Applicant amended claims (in German).
International Search Report for PCT/EP2018/072166 dated Oct. 5, 2018.
Written Opinion of the International Searching Authority for PCT/EP2018/072166 dated Oct. 5, 2018.

*Primary Examiner* — Jafar F Parsa
(74) *Attorney, Agent, or Firm* — Faegre Drinker Biddle & Reath LLP

(57) ABSTRACT

A process for preparing an ester of (meth)acrylic acid or a derivative thereof comprises reacting (meth)acrylic acid or a derivative thereof with glycerol carbonate at a reaction temperature of 10 to 150° C. without a solvent in the presence of at least one enzyme catalyzing the esterification reaction.

13 Claims, No Drawings

PROCESS FOR PRODUCING (METH)ACRYLATES FROM GLYCEROL CARBONATE

CROSS-REFERENCE TO RELATED APPLICATIONS

This application is a national stage application (under 35 U.S.C. § 371) of PCT/EP2018/072166, filed Aug. 16, 2018, which claims benefit of European Application No. 17186588.4, filed Aug. 17, 2017, both of which are incorporated herein by reference in their entirety.

The present invention relates to a process for preparing an ester of (meth)acrylic acid or a derivative thereof by reaction of (meth)acrylic acid or a derivative thereof with glycerol carbonate at a reaction temperature of 10 to 150° C. without a solvent in the presence of at least one enzyme catalyzing the esterification reaction, an ester obtainable by the process of the invention and also the method of using such an ester in contact lenses or as crosslinker or adhesion improver for dispersions employed with preference as adhesives, as paints, as textile, leather or paper auxiliaries and in curable coatings.

Processes for preparing esters of (meth)acrylic acid or a derivative thereof with glycerol carbonate are already known to the notional person skilled in the (prior) art.

WO 2013/129486 A1 discloses a process for preparing an ester of acrylic acid and glycerol carbonate by reaction of glycerol carbonate with vinyl acrylate in tert-butanol as solvent and in the presence of a lipase catalyzing the transesterification reaction.

N. Bassam et al., Green Chemistry, 2013, 15, 1900 to 1909 disclose a process for preparing glycerol carbonate acrylate by reaction of glycerol carbonate with acryloyl chloride in dichloromethane as solvent and in the presence of triethylamine.

Existing processes for preparing (meth)acrylic esters of glycerol carbonate are still improvable in their space-time yield. The purity of the glycerol carbonate (meth)acrylates obtained by the prior art processes is also still improvable.

It is an object of the present invention to provide a process for preparing esters of (meth)acrylic acid or a derivative thereof with glycerol carbonate without the abovementioned disadvantages. More particularly, the process shall provide the desired products in high yield, selectivity and purity.

We have found that these objects are achieved by the process which the present invention provides for preparing an ester of (meth)acrylic acid or a derivative thereof by reaction of (meth)acrylic acid or a derivative thereof with glycerol carbonate at a reaction temperature of 10 to 150° C. without a solvent in the presence of at least one enzyme catalyzing the esterification reaction.

We have found that these objects are specifically achieved by the process which the present invention provides for preparing an ester of (meth)acrylic acid by reaction of (meth)acrylic acid or $C_{1-12}$-alkyl(meth)acrylate with glycerol carbonate at a reaction temperature of 10 to 150° C. without a solvent in the presence of at least one enzyme catalyzing the esterification reaction.

The objects of the present invention are further achieved by the ester which is obtainable according to the present invention and also its use in contact lenses or as crosslinker or adhesion improver for dispersions employed with preference as adhesives, as paints, as textile, leather or paper auxiliaries and in curable coatings.

The process of the present invention will now be described in detail:

Esters of (meth)acrylic acid or a derivative thereof with glycerol carbonate are obtainable by the process of the present invention. The group of chemical compounds termed esters is known to the notional person skilled in the art. In an ester, a carbon-containing moiety replaces the proton in the carboxylic acid function of an organic carboxylic acid.

The process of the present invention comprises the reaction of (meth)acrylic acid or a derivative thereof with glycerol carbonate.

Useful starting materials for the process of the present invention include in general (meth)acrylic acid and any derivatives thereof known to the notional person skilled in the art. In the present invention, the term "(meth)acrylic acid" is used as a collective term for acrylic acid and methacrylic acid, i.e., the term describes acrylic acid, methacrylic acid or mixtures thereof.

(Meth)acrylic acid derivatives employed with preference as starting materials for the purposes of the present invention include the corresponding esters of acrylic acid, i.e., acrylates, or of methacrylic acid, i.e., methacrylates. In the present invention, the term "(meth)acrylic acid derivative" also comprehends (meth)acrylic acid derivatives having substituents other than hydrogen or methyl on the double bond. (Meth)acrylic esters employed in the process of the present invention are preferably saturated in the alcohol moiety, i.e., they do not contain any unsaturated C—C double or triple bonds.

In a particularly preferred embodiment of the process according to the present invention, the (meth)acrylic acid employed as starting compound or a derivative thereof, conforms to general formula (I)

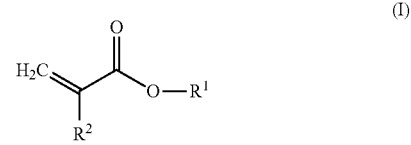

(I)

where $R^1$ and $R^2$ each independently have the following meanings:

$R^1$ is hydrogen, methyl, ethyl, propyl, for example n-propyl, $R^2$ is hydrogen, an aliphatic, linear or branched, saturated or unsaturated hydrocarbon moiety having altogether 1 to 24 carbon atoms and optionally comprising heteroatoms selected from N, O, P, S and/or optionally at least one functional group, or a cyclic, saturated or unsaturated hydrocarbon moiety having altogether 3 to 24 carbon atoms and optionally comprising heteroatoms selected from N, O, P, S and/or optionally at least one functional group or a substituted or unsubstituted aromatic hydrocarbon moiety having altogether 5 to 24 carbon atoms and optionally comprising heteroatoms selected from N, O, P, S, with or without functional groups, for example CN or $SO_3$.

Substituents optionally present on $R^2$ include, for example, alkyl chains of 1 to 6 carbon atoms. Functional groups optionally present as substituents on $R^2$ include, for example, hydroxyl, amino, keto, carbonyl, halide, cyano, isocyano and sulfate groups. In one preferred embodiment, $R^2$ is not substituted.

$R^1$ in general formula (I) is preferably selected from hydrogen or methyl.

$R^2$ in general formula (I) is preferably selected from hydrogen or methyl.

The present invention accordingly relates with preference to that process of the present invention wherein the (meth) acrylic acid derivative used is an ester, preferably $C_{1-12}$-alkyl(meth)acrylate, more preferably $C_{1-6}$-alkyl(meth)acrylate, especially a methyl, ethyl or propyl ester.

The compounds of the general formula which are employed with particular preference for the purposes of the present invention are those in which $R^1$ and $R^2$ are each hydrogen (acrylic acid), $R^1$ is hydrogen and $R^2$ is methyl (methacrylic acid), $R^1$ is methyl and $R^2$ is hydrogen (methyl acrylate) or $R^1$ and $R^2$ are each methyl (methyl methacrylate).

Mixtures comprising two or more compounds of general formula (I) are also employable for the purposes of the present invention.

Compounds of general formula (I) and/or mixtures thereof are obtainable by methods known to the notional person skilled in the art, or are commercially available.

Glycerol carbonate is employed in the process of the present invention as well as (meth)acrylic acid or a derivative thereof. Glycerol carbonate is known per se to the notional person skilled in the art and is depicted hereafter as compound (II):

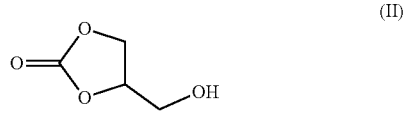

(II)

Glycerol carbonate is commercially available and is obtainable by methods known to the notional person skilled in the art, for example by reaction of glycerol with urea (EP955298), cyclic carbonates such as ethylene carbonate or propylene carbonate (EP0739888), linear carbonates such as, for example, diethyl carbonate or dimethyl carbonate (WO02010043581). Further possibilities are the reaction of glycerol with carbon monoxide (EP0582201), phosgene or carbon dioxide (WO2011042288) and also that of glycidol with carbon dioxide (WO 2010106324).

In one preferred embodiment of the process according to the present invention, the molar ratio of (meth)acrylic acid or a derivative thereof to glycerol carbonate is 2:1, up to 30:1, more preferably 4:1, up to 20:1 most preferably in the range from 5:1 to 10:1. The ratio of (meth)acrylic acid or a derivative thereof to glycerol carbonate is generally at most 100:1.

The high ratio of (meth)acrylic acid or a derivative thereof to glycerol carbonate makes it possible to eschew an entrainer, since the (meth)acrylic acid or the derivative thereof acts as an entrainer.

The process of the present invention is carried out at a reaction temperature of 10 to 100° C. In one preferred embodiment, the reaction temperature is in the range from 20 to 90° C., more preferably in the range from 30 to 70° C. and most preferably in the range from 40 to 60° C.

The process of the present invention is carried out in the presence of at least one enzyme catalyzing the esterification reaction. Enzymes useful for the purposes of the present invention are preferably hydrolases [EC 3.x.x.x], especially esterases [EC 3.1.x.x.] and proteases [EC 3.4.x.x]. Carboxyl ester hydrolases [EC 3.1.1.x] are preferred. Particular preference is given to using lipases as hydrolases. Especially lipases from *Achromobacter* sp., *Aspergillus* sp., *Burholderia* sp., *Candida* sp., *Mucor* sp., *Penicillium* sp., *Pseudomonas* sp., *Rhizopus* sp., *Thermomyces* sp. or porcine pancreas are used. The enzymes and their functions are described for example in Römpp Online, 2002, "Hydrolasen", "Lipasen" and "Proteasen".

It is particularly preferred in the present invention to use a lipase from *Candida Antarctica* (*Candida Antarctica* Lipase B) as enzyme.

The at least one enzyme is employed for the purposes of the present invention in an amount of 0.1 to 20 wt %, preferably from 0.5 to 10 wt % and more preferably from 0.7 to 5 wt %, all based on the glycerol carbonate present in the reaction mixture.

The at least one enzyme may be employed for the purposes of the present invention in mobilized or immobilized form. The preference of the present invention is for the use of immobilized enzymes, i.e., enzymes present on a carrier. Suitable carrier materials are known per se to the notional person skilled in the art; organic, polymeric carrier materials are employed in particular in order to immobilize the at least one enzyme used in the process of the present invention.

The present invention accordingly relates with preference to that process of the present invention wherein the at least one enzyme is present on a carrier material.

It is preferably on a suitable carrier that the enzyme is immobilized in the process of the present invention. The context is that there are in general five conventional ways to immobilize enzymes, namely adsorption, covalent bonding, membrane encapsulation, gel encapsulation, and crosslinking. Different carrier materials are employable for each, although the chemical interactions of the carrier surface with the enzyme have to be aligned so as not to produce any adverse side-effects, for example deactivation. Useful solid carriers include in principle various inorganic and organic materials, and the latter may be of natural or synthetic origin. Inorganic carriers usually have a high level of compressive stability, while organic carriers exhibit a high level of chemical stability. The inorganic carriers used are predominantly porous materials based on silicas or aluminas and/or mixtures thereof. Natural organic carriers include, for example, polysaccharides, e.g., cellulose, starch, dextran, agarose and chitin. But proteins, such as collagen, gelatin and albumin, may also find application. Useful synthetic organic polymers include poly(meth)acrylates, polyacrylamides, vinyl and allyl polymers, polyesters or polyamides.

One example of a carrier material used with particular preference is a macroporous, divinylbenzene-crosslinked methacrylate-based polymer in spherical bead form. This carrier material used with preference has a particle size ($D_{80}$) of 0.3 to 1.5 mm, preferably 0.31 to 1.2 mm, and an effective size of 0.3 to 0.6 mm, preferably 0.3 to 0.5 mm. The density of the carrier material used with preference is for example in the range from 1.0 to 1.5 g/ml, preferably from 1.02 to 1.1 g/ml. The water content of the carrier material used with preference is for example in the range from 40 to 80 wt %, preferably from 50 to 70 wt %.

The BET surface area of the organic carrier material used with preference for the purposes of the present invention is for example in the range from 100 to 200 $m^2/g$, preferably from 110 to 150 $m^2/g$.

The pore volume of the carrier material used with preference for the purposes of the present invention is for example in the range from 0.2 to 1.0 $cm^3/g$, preferably from 0.4 to 0.8 $cm^3/g$.

The pore diameter of the pores present in the carrier material used with preference for the purposes of the present invention is for example in the range from 5 to 50 nm, preferably from 10 to 30 nm.

Enzymes employed with particular preference in the process of the present invention are already immobilized on a suitable carrier. Thus immobilized enzymes, preferably lipases, are available from Novozymes under the tradename of Novozym® 435 (lipase from *Candida antarctica* B).

In the preferred embodiment, wherein the at least one enzyme is present on a carrier material, it is generally present in an amount of 1 to 20 wt %, preferably 2 to 15 wt % and more preferably 5 to 12 wt %, all based on the combined total of enzyme and carrier material.

The enzymes employed in the process of the present invention as being capable of catalyzing the esterification reaction are also obtainable in situ in the process from corresponding organisms. Useful organisms for this purpose include any naturally occurring or genetically modified microorganisms, unicellular entities or cells that catalyze the esterification or transesterification reaction via a hydrolase [EC 3.x.x.x], preferably an esterase [EC 3.1.x.x.] or protease [EC 3.4.x.x], preferably a carboxyl ester hydrolase [EC 3.1.1.x] and especially a lipase. Any organisms comprising hydrolases and known to the notional person skilled in the art are usable. Preference is given to using organisms comprising lipases as hydrolases. Especially *Achromobacter* sp., *Aspergillus* sp., *Burholderia* sp., *Candida* sp., *Mucor* sp., *Penicillium* sp., *Pseudomonas* sp., *Rhizopus* sp., *Thermomyces* sp. and cells from porcine pancreas find use.

The organisms in question may be the unchanged organisms themselves or genetically modified organisms which originally express the enzymes insufficiently, if at all, and display a sufficiently high level of enzyme activity and productivity only once modified. Genetic modification may further be used to align the organisms with the reaction conditions and/or cultivation conditions.

The process of the present invention is carried out without a solvent. "Without a solvent" is to be understood in the context of the present invention as meaning that besides the substrates present, i.e., (meth)acrylic acid or a derivative thereof and glycerol carbonate, the at least one enzyme, optionally at least one stabilizer and optionally at least one drier, no further organic or aqueous solvent is present in the reaction mixture.

Reaction products formed in the course of the esterification or transesterification reaction of the present invention include, for example, water from the use of corresponding (meth)acrylic acids or alcohols, for example methanol, ethanol, propanol, from use of the corresponding esters, especially (meth)acrylic esters. To further raise the reaction rate by shifting the chemical equilibrium, the preference in the present invention is that the water formed during the reaction, or the corresponding alcohols, be removed in a continuous manner.

Continuous removal of the water formed during reaction, or of the corresponding alcohols, may in general be effected by any method known to the notional person skilled in the art, for example employing a drier, a hydrophobic membrane, distillative removal and combinations thereof.

According to the invention, therefore, the present invention relates with preference to that process of the present invention which is carried out in the presence of a drier. Useful driers for the purposes of the present invention are known per se to the notional person skilled in the art, being selected for example from the group consisting of molecular sieves, calcium chloride, blue gel, magnesium sulfate and mixtures thereof.

In one preferred embodiment of the process according to the present invention, especially when said process is being carried out on a comparatively large scale, for example in a pilot plant or on an industrial scale, water, alcohols, for example methanol, ethanol and/or propanol, or mixtures thereof are removed during the reaction by distillation. Appropriate apparatus is known per se to the notional person skilled in the art, for example in the form of distillation columns.

In one preferred embodiment of the process according to the present invention, said process is carried out in the presence of at least one stabilizer. It is further preferred to use a stabilizer in order to control the polymerization tendency of the starting materials used, i.e., of (meth)acrylic acid or a derivative thereof, and/or of the products formed during the reaction, i.e., of the esters of glycerol carbonate with (meth)acrylic acid or a derivative thereof.

Useful stabilizers and/or polymerization inhibitors include, for example, N-oxides (nitroxyl or N-oxyl radicals, i.e., compounds having at least one >N—O group), e.g., 4-hydroxy-2,2,6,6-tetramethylpiperidine N-oxyl, 4-oxo-2,2, 6,6-tetramethylpiperidine N-oxyl, 4-acetoxy-2,2,6,6-tetramethylpiperidine N-oxyl, 2,2,6,6-tetramethylpiperidine N-oxyl, 4,4',4"-tris(2,2,6,6-tetramethylpiperidine N-oxyl) phosphite or 3-oxo-2,2,5,5-tetramethylpyrrolidine N-oxyl; mono- or polyhydric phenols with or without one or more alkyl groups, for example alkylphenols, e.g., o-, m- or p-cresol (methylphenol), 2-tert-butylphenol, 4-tert-butylphenol, 2,4-di-tert-butylphenol, 2-methyl-4-tert-butylphenol, 2-tert-butyl-4-methylphenol, 2,6-tert-butyl-4-methylphenol, 4-tert-butyl-2,6-dimethylphenol or 6-tert-butyl-2,4-dimethylphenol; quinones, e.g., hydroquinone, hydroquinone monomethyl ether, 2-methylhydroquinone or 2,5-di-tert-butylhydroquinone; hydroxyphenols, for example pyrocatechol (1,2-dihydroxybenzene) or benzoquinone; aminophenols, e.g., p-aminophenol; nitrosophenols, e.g., p-nitrosophenol; alkoxyphenols, e.g., 2-methoxyphenol (guaiacol, pyocatechol monomethyl ether), 2-ethoxyphenol, 2-isopropoxyphenol, 4-methoxyphenol (hydroquinone monomethyl ether), mono- or di-tert-butyl-4-methoxyphenol; tocopherols, e.g., a-tocopherol and also 2,3-dihydro-2, 2-dimethyl-7-hydroxy-benzofuran (2,2-dimethyl-7-hydroxycoumaran), aromatic amines, e.g., N,N-diphenylamine or N-nitrosodiphenylamine; phenylenediamines, for example N,N'-dialkyl-p-phenylenediamine, wherein the alkyl moieties may be the same or different and may each independently consist of 1 to 4 carbon atoms and be straight-chain or branched, e.g., N,N'-dimethyl-p-phenylenediamine or N,N'-diethyl-p-phenylenediamine, hydroxylamines, e.g., N,N-diethylhydroxylamine, imines, e.g., methylethylimine or methylene violet, sulfonamides, e.g., N-methyl-4-toluenesulfonamide or N-tert-butyl-4-toluenesulfonamide, oximes, such as aldoximes, ketoximes or amidoximes, e.g., diethyl ketoxime, methyl ethyl ketoxime or salicylaldoxime, phosphorus compounds, for example triphenylphosphine, triphenyl phosphite, triethyl phosphite, hypophosphorous acid or alkyl esters of phosphorous acids; sulfur compounds such as, for example, diphenyl sulfide or phenothiazine; metal salts, such as copper or manganese, cerium, nickel, chromium salts, for example metal chlorides, sulfates, salicylates, tosylates, acrylates or acetates, e.g., copper acetate, copper(II) chloride, copper salicylate, cerium(II) acetate or cerium(III) ethylhexanoate, or mixtures thereof.

Very useful stabilizers for the process according to the present invention are hydroquinone, hydroquinone monomethyl ether (MEHQ), phenothiazine, 4-hydroxy-2,2,6,6-tetramethylpiperidine N-oxyl, 4-oxo-2,2,6,6-tetramethylpiperidine N-oxyl, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol, 2-methyl-4-tert-butylphenol, hypophosphorous acid, copper acetate, copper(II) chloride, copper salicylate and cerium(III) acetate. Hydroquinone monomethyl ether (MEHQ) and/or phenothiazine (PTZ) are particularly preferred stabilizers.

The amounts in which a suitable polymerization inhibitor is used range in general from 1 to 10 000 ppm, preferably from 10 to 5000 ppm, more preferably from 30 to 2500 ppm and especially from 50 to 1500 ppm, all based on the unsaturated monomers and reckoned per individual substance.

The process of the present invention may generally be carried out at a pressure of 0.01 to 1.5 bar (a). In one preferred embodiment, the process according to the present invention is carried out at atmospheric pressure.

It is further preferred to carry out the process at a pressure below atmospheric pressure, i.e., at a pressure of 0.01 to about 0.9 bar (a). In the preferred embodiment, viz., the resultant water and/or low molecular weight alcohols are continuously removed by distillation during the process of the present invention, the process is specifically carried out at a pressure of 0.01 to 0.5 bar (a) in order to further lower the boiling point of the low molecular weight compounds formed.

After reaction, the reaction mixture obtained may generally be worked up according to any method known to the notional person skilled in the art, examples being filtration, distillative removal of excess substrates, etc.

The products obtained according to the present invention conform to general formula (III)

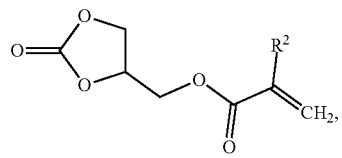
(III)

where $R^2$ has the same meanings as itemized for the compound of general formula (I).

$R^2$ in the compound of general formula (III) is preferably hydrogen or methyl.

The present invention further also provides a corresponding ester obtainable, preferably obtained, by the process of the present invention, especially the compounds of general formula (III). The esters obtained according to the present invention, especially the compounds of general formula (III), are notable for a particularly high level of purity. Owing to this high purity, the compounds obtained according to the present invention are useful without further purification.

In one further embodiment of the process according to the present invention, the resulting glycerol carbonate (meth)acrylate or a derivative thereof is converted into glycerol mono(meth)acrylate or a derivative thereof after the reaction.

This optional step of the process according to the present invention comprises cleaving off the protective carbonate group in order that the two hydroxyl groups may thereby be obtained in free form. The product of this optional cleaving step is a glycerol mono(meth)acrylate ester or a derivative thereof, hereafter depicted as general formula (IV):

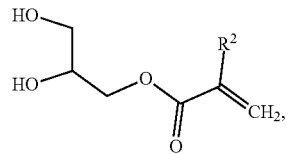
(IV)

where $R^2$ has the same meanings as itemized for the compound of general formula (I).

$R^2$ in the compound of general formula (IV) is preferably hydrogen or methyl.

The optional cleaving step in the process of the present invention may in general be carried out according to any methods known to the notional person skilled in the art, for example by mild alkaline hydrolysis. Suitable methods are found in T. W. Greene, Protective Groups in Organic Synthesis, Second Edition 1991, John Wiley & Sons Inc., pp. 108, 109, 140, 141.

The present invention further also provides the esters obtainable by that process of the present invention which comprises the step of cleaving off the protective carbonate group. These compounds obtainable, preferably obtained, according to the present invention are notable versus corresponding compounds obtained by prior art processes for explicit monofunctionalization, i.e., the absence of glycerol di(meth)acrylates.

The present invention more particularly provides the following compounds:

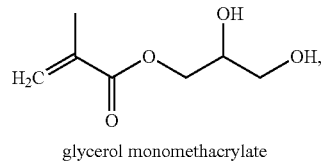
(IVa)

glycerol monomethacrylate

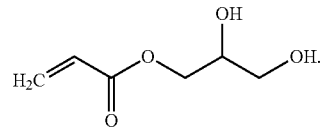
(IVb)

glycerol monoacrylate

The present invention more preferably provides glycerol mono(meth)acrylates. The process of the present invention provides glycerol mono(meth)acrylates in a very particularly high purity, i.e., substantially free from glycerol di(meth)acrylate. A preferred embodiment of the present invention provides glycerol mono(meth)acrylate in a high purity.

The present invention accordingly also provides the method of using an ester of the present invention, especially glycerol mono(meth)acrylate ester, in contact lenses or as crosslinker or adhesion improver for dispersions employed with preference as adhesives, as paints, as textile, leather or paper auxiliaries and in curable coatings.

EXAMPLES

Novozym® 435 enzyme is used in all runs. It is a lipase from *Candida antarctica* on a macroporous, divinylbenzene-crosslinked methacrylate-based polymer in spherical bead form. The carrier material has a particle size ($D_{80}$) of 0.315 to 1.0 mm and an effective size of 0.32 to 0.45 mm. The density is 1.06 g/ml; the water content is 55 to 65 wt %. The BET surface area of the carrier material is 130 m$^2$/g. The pore volume of the carrier material is 0.5 cm$^3$/g. The pore diameter of the pores present in the carrier material is 15 nm.

Example 1 (without Molecular Sieve)

Glycerol carbonate (4.0 g, 0.034 mol), methyl acrylate (15.0 g, 0.174 mol), MeHQ (ca. 400 ppm), Novozym® 435 (0.4 g, 10 wt %) were weighed into a 50 ml Schott flask. The batch was shaken in a water bath shaker at 40° C. Conversion was policed by GC. The results after 2 h, 4 h and 8 h are shown in Table 1:

TABLE 1

|  | 2 h [area %] | 4 h [area %] | 8 h [area %] |
|---|---|---|---|
| glycerol carbonate | 50.50 | 45.50 | 44.50 |
| glycerol carbonate acrylate | 49.50 | 54.50 | 55.50 |

Example 2 (with Molecular Sieve)

Glycerol carbonate (4.0 g, 0.034 mol), methyl acrylate (15.0 g, 0.174 mol), MeHQ (ca. 400 ppm), Novozym® 435 (0.4 g, 10 wt %) and 5 A molecular sieve (9 g) were weighed into a 50 ml Schott flask. The batch was shaken in a water bath shaker at 40° C. Conversion was policed by GC. The results after 2 h, 4 h and 8 h are shown in Table 2:

TABLE 2

|  | 2 h [area %] | 4 h [area %] | 8 h [area %] |
|---|---|---|---|
| glycerol carbonate | 58.50 | 17.10 | <1 |
| glycerol carbonate acrylate | 41.50 | 82.90 | >99 |

Example 3 (Scaled-Up Experiment)

Glycerol carbonate (1000 g, 8.46 mol), methyl acrylate (3645 g, 42.34 mol), MeHQ (400 mg) and Novozym® 435 (75 g, 7.5 wt %) were weighed into a 10 L HWS Miniplant reactor. This was followed by stirring at 40° C., 195 mbar and 140 rpm. Methanol was continuously removed from the methanol/methyl acrylate azeotrope by distillation. Conversion was policed by GC. The results after certain times are shown in Table 3:

TABLE 3

| Time [h] | Time [min] | Reactant [area %, RT time: 6.048'] | Product [area %, RT time: 6.867'] |
|---|---|---|---|
| 0 | 0 | 94.1 | 0 |
| 2.00 | 120 | 40.99 | 59 |
| 4.00 | 240 | 27.87 | 72.12 |
| 6.00 | 360 | 18.97 | 81.02 |
| 9.00 | 540 | 13.73 | 86.26 |
| 11.00 | 660 | 11.54 | 88.45 |
| 14.00 | 840 | 9.18 | 90.81 |
| 16.00 | 960 | 8.21 | 91.78 |
| 18.00 | 1080 | 6.41 | 93.58 |
| 20.00 | 1200 | 6.05 | 93.94 |
| 23.00 | 1380 | 4.27 | 95.72 |
| 25.00 | 1500 | 3.63 | 96.36 |

Example 4 (Scaled-Up Experiment)

Glycerol carbonate (600 g, 5.08 mol), methyl acrylate (4374 g, 50.81 mol), MeHQ (250 mg) and Novozym® 435 (45 g, 7.6 wt %) were weighed as fixed bed into a 10 L HWS Miniplant reactor. The reaction mixture was continuously pumped through this fixed bed until the reaction had ended. The conditions were 50° C., 195 mbar and 140 rpm. Methanol was continuously removed from the methanol/methyl acrylate azeotrope by distillation. Conversion was policed by GC. The results after certain times are shown in Table 4:

Table 4:

TABLE 4

| Time [h] | Time [min] | Reactant [area %, RT time: 6.048'] | Product [area %, RT time: 6.867'] |
|---|---|---|---|
| 0.00 | 0 | 96.34 | 0 |
| 1.00 | 60 | 32.91 | 67.08 |
| 2.00 | 120 | 24.2 | 75.79 |
| 4.00 | 240 | 13.61 | 86.38 |
| 5.00 | 300 | 13.69 | 86.3 |
| 6.00 | 360 | 8.85 | 91.14 |
| 8.00 | 480 | 6.01 | 93.98 |
| 10.00 | 600 | 3.67 | 96.32 |
| 12.00 | 720 | 3.30 | 96.69 |
| 14.00 | 840 | 2.81 | 97.48 |
| 15.00 | 900 | 1.42 | 98.57 |

We claim:

1. The process for preparing an ester of (meth)acrylic acid or a derivative thereof by reaction of (meth)acrylic acid or an ester thereof with glycerol carbonate at a reaction temperature of 10 to 150° C. without a solvent in the presence of at least one enzyme catalyzing the esterification reaction.

2. The process according to claim 1 wherein the reaction temperature is in the range from 10 to 100° C.

3. The process according to claim 1, wherein the enzyme used is a lipase from *Candida antarctica*.

4. The process according to claim 1, wherein the at least one enzyme is present on a carrier material.

5. The process according to claim 1, wherein the (meth) acrylic acid ester used is a $C_{1-12}$-alkylester.

6. The process according to claim 1, in the presence of a drier.

7. The process according to claim 1, in the presence of at least one stabilizer.

8. The process according to claim 1, wherein water, alcohols or mixtures thereof are removed during the reaction by distillation.

9. The process according to claim 1, wherein the molar ratio of (meth)acrylic acid or an ester thereof to glycerol carbonate is in the range from 2:1 to 30:1.

10. The process according to claim 1, wherein the resulting glycerol carbonate (meth)acrylate is converted into glycerol mono(meth)acrylate after the reaction.

11. The process according to claim 1, wherein the reaction temperature is in the range from 20 to 90° C.

12. The process according to claim 1, wherein the reaction temperature is in the range from 40 to 60° C.

13. The process according to claim 1, wherein the (meth)acrylic acid ester used is a methyl, ethyl or propyl ester.

* * * * *